US008173200B2

(12) United States Patent
Davis et al.

(10) Patent No.: US 8,173,200 B2
(45) Date of Patent: May 8, 2012

(54) SELECTIVE APPLICATION OF THERAPEUTIC AGENT TO A MEDICAL DEVICE

(75) Inventors: Liza J. Davis, St. Michael, MN (US); Thomas Priebe, Shakopee, MN (US); Kim Robertson, Forest Lake, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1041 days.

(21) Appl. No.: 12/113,993

(22) Filed: May 2, 2008

(65) Prior Publication Data

US 2008/0274266 A1 Nov. 6, 2008

Related U.S. Application Data

(60) Provisional application No. 60/915,505, filed on May 2, 2007.

(51) Int. Cl.

| | |
|---|---|
| ***A61L 33/00*** | (2006.01) |
| ***B05D 3/00*** | (2006.01) |
| ***A61K 9/50*** | (2006.01) |
| ***A61K 9/28*** | (2006.01) |
| ***A61M 25/00*** | (2006.01) |
| ***A41D 19/00*** | (2006.01) |
| ***B01J 13/00*** | (2006.01) |

(52) U.S. Cl. .................... 427/2.24; 427/2.25; 427/2.21; 427/2.28; 427/2.1; 427/2.3; 427/2.14; 427/352

(58) Field of Classification Search ................. 427/2.24, 427/2.1, 2.25, 2.21, 2.28, 2.3, 2.14, 352
See application file for complete search history.

(56) References Cited

U.S. PATENT DOCUMENTS

| | | | | |
|---|---|---|---|---|
| 5,091,205 | A | | 2/1992 | Fan |
| 5,679,400 | A | * | 10/1997 | Tuch ........................... 427/2.14 |
| 6,063,339 | A | | 5/2000 | Tisone et al. |
| 6,395,326 | B1 | | 5/2002 | Castro et al. |
| 2005/0163913 | A1 | | 7/2005 | Spencer et al. |
| 2007/0281071 | A1 | | 12/2007 | Eidenschink et al. |

FOREIGN PATENT DOCUMENTS

WO 01/91918 A1 12/2001

* cited by examiner

*Primary Examiner* — Timothy J. Kugel
*Assistant Examiner* — Atnaf Admasu
(74) *Attorney, Agent, or Firm* — Kenyon & Kenyon LLP

(57) ABSTRACT

A method of coating an implantable medical device may include providing an implantable medical device, applying a polymer base to the medical device, and directing a first solution including therapeutic agent and solvent through the nozzle onto a target zone of the polymer base coating to penetrate the polymer base coating. The solution may be directed at the target zone until a predetermined concentration of the therapeutic agent can be integrated within the polymer base coating.

23 Claims, 8 Drawing Sheets

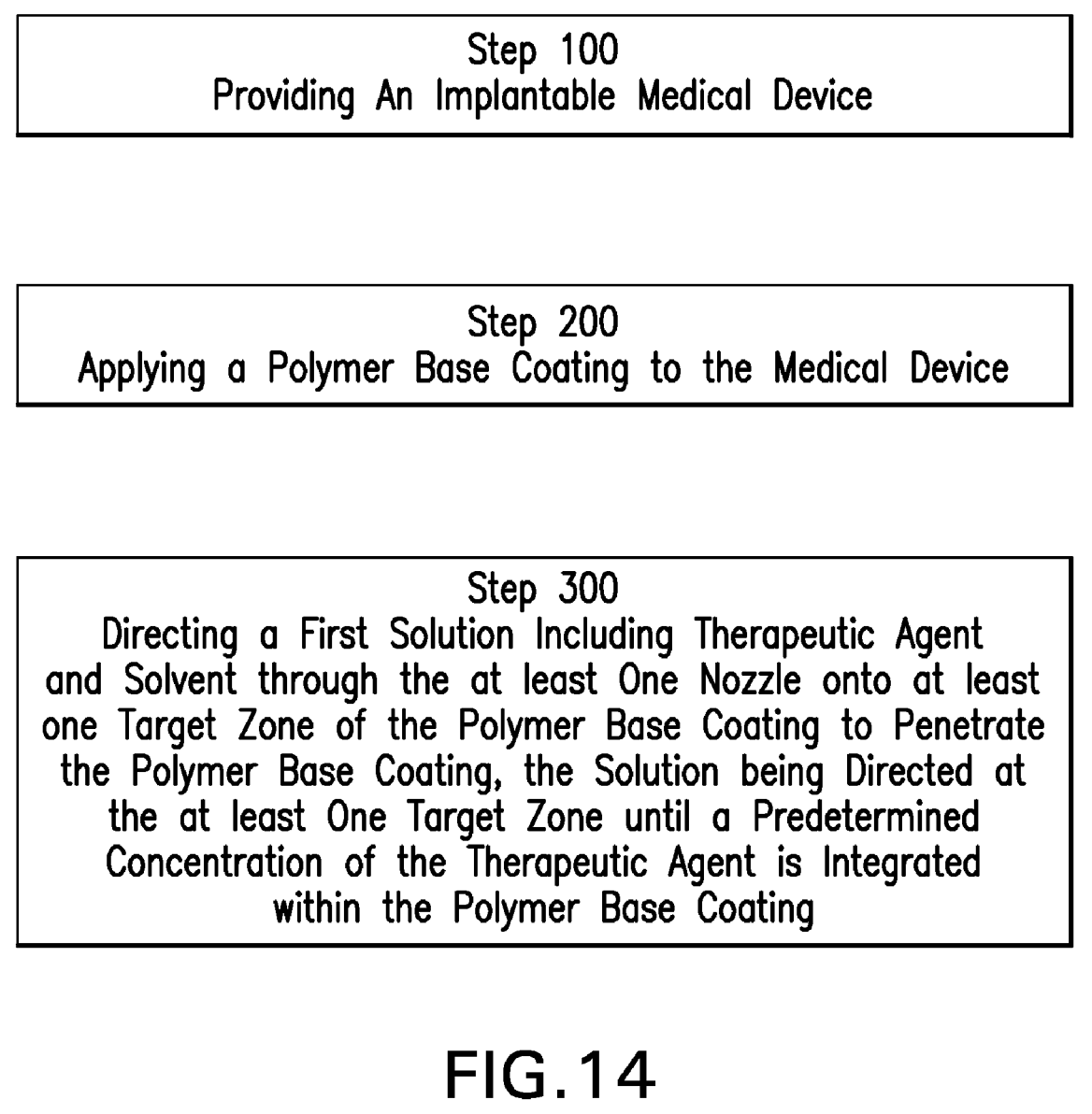

Step 100
Providing An Implantable Medical Device

Step 200
Applying a Polymer Base Coating to the Medical Device

Step 300
Directing a First Solution Including Therapeutic Agent and Solvent through the at least One Nozzle onto at least one Target Zone of the Polymer Base Coating to Penetrate the Polymer Base Coating, the Solution being Directed at the at least One Target Zone until a Predetermined Concentration of the Therapeutic Agent is Integrated within the Polymer Base Coating

FIG.14

SELECTIVE APPLICATION OF THERAPEUTIC AGENT TO A MEDICAL DEVICE

CROSS REFERENCE TO RELATED APPLICATION

The present application claims priority to U.S. provisional application Ser. No. 60/915,505 filed May 2, 2007, the disclosure of which is incorporated herein by reference in its entirety.

TECHNICAL FIELD

The present invention generally relates to the application of therapeutic agents to a medical device, such as a stent.

BACKGROUND

The positioning and deployment of medical devices within a target site of a patient is a common procedure of contemporary medicine. These devices, which may be implantable stents, chronic rhythm management leads, neuromodulation devices, implants, grafts, defibrillators, filters, catheters and other devices that may be deployed for short or sustained periods of time, may be used for many medical purposes. These can include the reinforcement of recently re-enlarged lumens, the replacement of ruptured vessels, and the treatment of disease, such as vascular disease by local pharmacotherapy, e.g., delivering therapeutic agent doses to target tissues while minimizing systemic side effects. The targeted delivery areas may include body lumens such as the coronary vasculature, esophagus, trachea, colon, biliary tract, urinary tract, prostate, brain, and the like.

Coatings may be applied to the surfaces of these medical devices to increase their effectiveness. These coatings may provide a number of benefits including reducing the trauma suffered during the insertion procedure, facilitating the acceptance of the medical device into the target site, and improving the post-procedure effectiveness of the device.

Coated medical devices may also provide for the localized delivery of therapeutic agents to target locations within the body. Such localized drug delivery avoids the problems of systemic drug administration, such as producing unwanted effects on parts of the body which are not to be treated, or not being able to deliver a high enough concentration of therapeutic agent to the afflicted part of the body. Localized drug delivery may be achieved, for example, by coating the entire outer surface of the medical device or just those portions of the medical device that directly contact the desired treatment site, such as the inner vessel wall. This drug delivery may be intended for short and/or sustained periods of time.

BRIEF DESCRIPTION

The present invention generally relates to the application of coating materials, including coating materials containing a therapeutic agent, to medical devices.

In accordance with certain embodiments of the present invention, an implantable medical device may be provided. This device may be expandable from an unexpanded position to an expanded position and may be carried on or supported by a delivery device such as an elongated catheter.

The medical device may be coated on one or more surfaces and this coating may contain a therapeutic agent. The therapeutic agent may be applied to or coated on the device in a selective manner such that it only covers portions of the device, has higher concentrations in some zones of the device than in others, and/or is positioned at different or selected depths of a coating of the device. Other selected deposition features may be used as well. This selective application of the therapeutic agent may be accomplished with precision dispensing devices as well as with the use of solvents.

In accordance with certain embodiments of the present invention, a method of coating an implantable medical device may include providing an implantable medical device, applying a polymer base coating to the medical device, and directing a first solution including therapeutic agent and solvent through the nozzle onto a target zone of the polymer base coating to penetrate the polymer base coating. The solution may be directed at the target zone until a predetermined concentration of the therapeutic agent can be integrated within the polymer base coating.

Also in accordance with certain embodiments of the present invention, a method of coating an implantable medical device may include providing an implantable medical device, positioning a delivery device having first, second, and third or more nozzles proximate to the medical device, applying a polymer base coating through the first nozzle to the medical device, and directing a first solution including therapeutic agent and solvent through the second nozzle onto a target zone of the polymer base coating to penetrate the polymer base coating. The solution may be directed at the target zone until a predetermined concentration of the therapeutic agent can be integrated within the polymer base coating.

Still in accordance with certain embodiments of the present invention, a method of coating a stent may comprise providing a stent having a lattice comprised of a plurality of struts, each strut having an inner surface, an outer surface, and a plurality of cut faces, applying a polymer base coating onto a target portion of the lattice portion, and directing a solution including therapeutic agent and solvent towards at least one first target zone of the polymer base coating to penetrate the polymer base coating. The solution may be directed at the first target zone until a predetermined concentration of the therapeutic agent can be integrated within the polymer base coating.

The invention may be embodied in numerous devices and through numerous methods and systems. The following detailed description, taken in conjunction with the annexed drawings, discloses examples of the invention. Other embodiments, which incorporate some, all or more of the features as taught herein, are also possible.

BRIEF DESCRIPTION OF THE DRAWINGS

Referring to the drawings, which form a part of this disclosure:

FIG. 14 shows method steps for selectively applying coating materials to a medical device in accordance with certain embodiments of the present invention.

DETAILED DESCRIPTION

The present invention generally relates to the selective application of therapeutic agents to a medical device. This may include applying therapeutic agent to medical devices such as implantable stents, chronic rhythm management leads, neuromodulation devices, implants, grafts, defibrillators, filters, and catheters.

Certain embodiments of the present invention regard the application of therapeutic agents in at least a two-step process so that various therapeutic agent distribution patterns may be achieved independently of the medical device geometry.

For example, in a conventional coating application for a stent, a polymer, therapeutic agent, and solvent are uniformly applied at the same time over the length the stent. Consequently, in the conventional stent coating process, therapeutic agent distribution patterns may be substantially dictated by stent geometry. However, as therapeutic agent delivery and dosage become increasingly important with drug eluting stents, there is a developing need for coating processes which optimize therapeutic agent delivery irrespective of stent geometry.

To address this need for improved coating processes for medical devices, certain embodiments of the present invention may utilize at least a two-step coating process for applying therapeutic agents. In the first step, a polymer base coating can be applied. Then, in at least a second separate step, at least one therapeutic agent and solvent solution can be applied selectively over the length of the medical device utilizing a targeted delivery device (e.g., a drop-on-demand device) to achieve a desired therapeutic agent distribution pattern. It is noted, in other embodiments, the base coating may include therapeutic agent.

In addition, the solvent may be selected such that the therapeutic agent may be completely soluble and the base polymer can be partially or fully soluble. Coating process parameters (e.g., droplet size, nozzle distance, etc.) and solvent solution selection may then be used to control the depth of penetration of the therapeutic agent into the polymer base coating. The therapeutic agent distribution pattern may control the rate, duration, and dosage of therapeutic agent release.

Also in accordance with certain embodiments of the present invention, therapeutic agent may be increased in specialized regions of the medical device geometry (e.g., apices of a stent) or decreased in others (e.g., segments of a stent). Likewise, different types and combinations of therapeutic agents may be applied over the length of the medical device.

Figure 1:
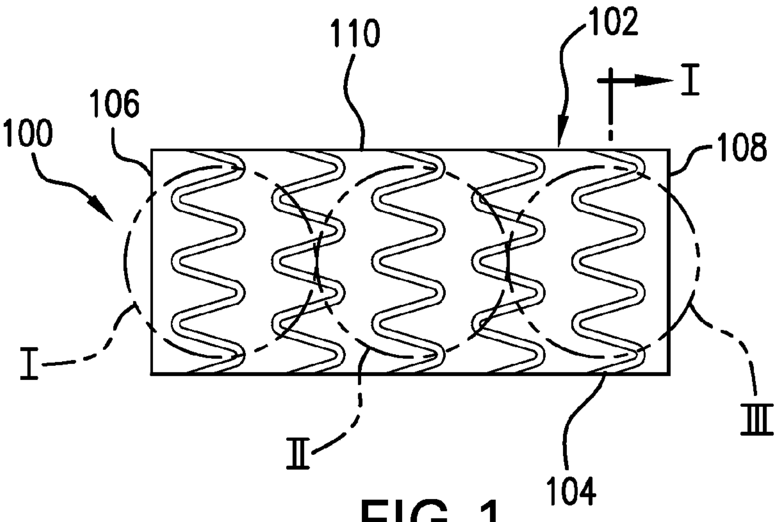
FIG. 1 shows a side-view of a coronary stent that may be employed in accordance with certain embodiments of the present invention.

FIG. 1 is a side view of an implantable coronary stent 100 that may be coated in accordance with certain embodiments of the present invention. The stent 100 may be comprised of a lattice 102 having a plurality of struts 104. The stent 100 may include a first end 106, a second end 108, and a middle portion 110. The struts 104 from FIG. 1 are shown in greater detail in FIGS. 2*a*-2*b*. The stent 100 may be self-expanding, mechanically expandable, or a hybrid stent which may have both self-expanding and mechanically expandable characteristics. In these examples, the stent 100 may be made up of a plurality of rounded bends 112 which have apices 114 and may be joined by segments 116.

Figure 2A:
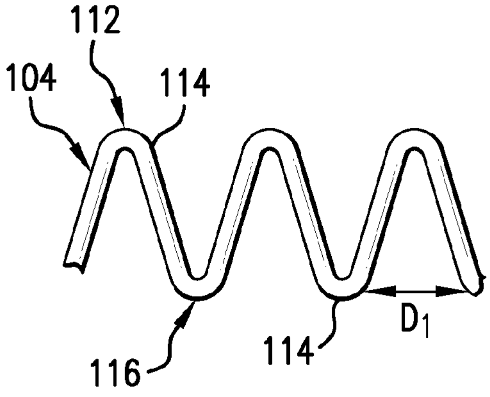
FIGS. 2*a-b* show the coronary stent of FIG. 1 in the unexpanded and expanded positions, respectively.
Figure 2B:
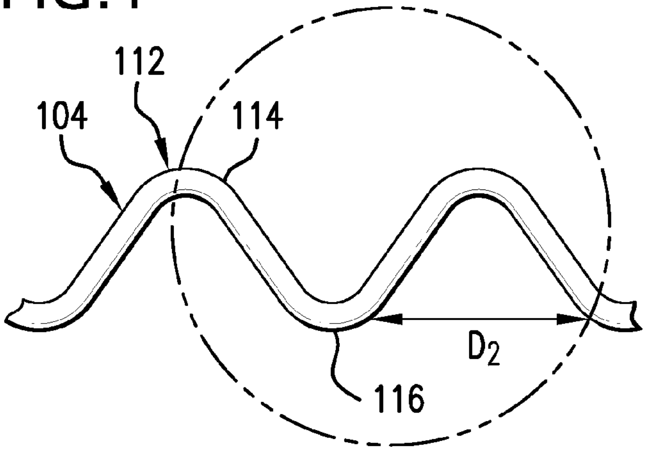

When the stent 100 is expanded, the distance between adjacent apices increases. For example, as seen in FIG. 2*a* a portion of the lattice portion 102 of the stent 100 of FIG. 1 is shown in an unexpanded position. In the unexpanded position, the distance $D_1$ is smaller than the distance $D_2$ when the stent is in an expanded position. For instance, the surface area of tissue covered by zone A in FIG. 2A may be smaller than the surface area of tissue covered by zone B in FIG. 2B after the stent has expanded. In other words, the diameter of the stent increases as the stent expands. Thus, any therapeutic agent applied to zone A will have a first concentration per area when the area of the zone is small and a second lower concentration per area when the zone has expanded as shown in zone B. When the therapeutic agent is applied to the stent 100 it may be applied in various concentrations along the surface of the stent such that after the stent is expanded the concentration of the therapeutic agent is uniform across the entire surface or a desired area of the stent.

The medical implant may be made from a variety of materials, including bio-ceramics, ceramics, plastics and metals. In addition, while the device shown in these initial figures is a stent, many other devices may be coated in accordance with the invention. For example, as stated herein above, other medical devices that may be coated include cardiac rhythm management leads, neuromodulation devices, implants, grafts, defibrillators, filters, catheters, and other devices used in connection with coating materials including therapeutic agent.

Figure 3A:
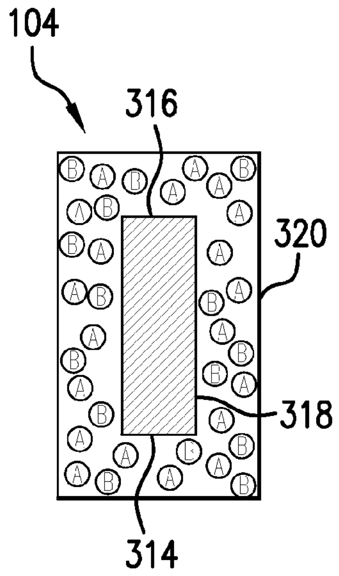
FIGS. 3*a-c* are enlarged cross-sectional side-views of the struts of FIG. 1 showing various coating material arrangements and concentrations that may be applied to a medical device in accordance with certain embodiments of the present invention.
Figure 3B:
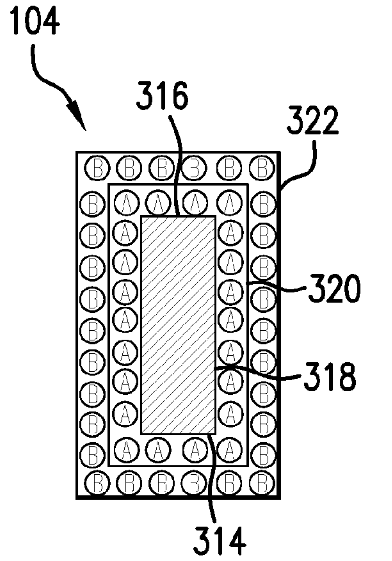
Figure 3C:
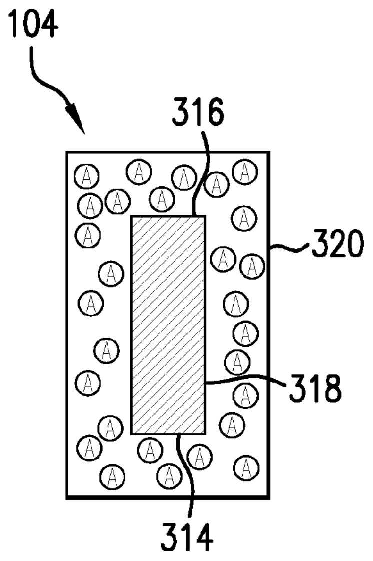

FIGS. 3*a-c* are enlarged side cross-sectional views of the struts of the stent of FIG. 1 that have been coated with various coating arrangements and concentrations in accordance with certain embodiments of the present invention. For example, FIG. 3*a* is a side view of a strut of section I of FIG. 1, FIG. 3*b* is a side view of a strut of section II of FIG. 1, and FIG. 3*c* is a side view of a strut of section III of FIG. 1.

The struts 104 in FIG. 3*a-c* have an inwardly facing surface 314, an outwardly facing surface 316, and two cut faces 318. Also shown on the struts 304 is a base coating 320 including a therapeutic agent generally designated as A. In FIGS. 3*a-c*, the base coating 320 is a polymer; however, any suitable base coating 320 which may be solubilized in solvent can be used. As can be seen in these examples, the base coating 320 covers the strut conformally. In other words, the base coating 320 covers at least portions of the inwardly facing surface 314, the outwardly facing surface 316, and the cut faces 318. Also as seen in FIG. 3*a*, a second therapeutic agent generally designated as B may also penetrate the base coating.

As also can be seen in FIG. 3*b*, the base coating 320 may be in contact with the strut 304 while a second coating 322, in this case a coating which also may be solubilized in solvent, includes a second therapeutic agent generally designated as B. The second coating 322 is in contact with the base coating 320. In this example, the second coating 322 covers the entire periphery of the base coating 320; however, it is noted that in certain embodiments of the present invention, the second coating 322 may cover only the outwardly facing or abluminal surface 316 of the strut 304.

In these examples, the base coating 320 containing therapeutic agent A may completely dissolve within the solution including solvent and therapeutic agent A. Accordingly, therapeutic agent A can penetrate the entire thickness of base coating 320 and may be highly concentrated through the entire thickness. In contrast, the second coating 322 may only partially dissolve within the solution including solvent and therapeutic agent B. Therefore, therapeutic agent B, in these examples, may not penetrate the entire thickness of the second coating 322 and can be concentrated near the free surfaces (e.g., the sides opposite to the medical device-base coating interface or the base coating-second coating interface) of the base and second coatings 320, 322.

FIG. 3*c* shows still another example in which only therapeutic agent A is located in the base coating 320. In this example, therapeutic agent B is not provided at all in the base coating 320.

It is contemplated that in other embodiments of the invention other arrangements for base and second coatings 320, 322, as well as therapeutic agent concentrations, are possible.

The base and second coatings 320, 322 may be applied in accordance with the processes and methods of the present invention (e.g., FIGS. 4, 5, 7, and 10). They may also be applied with different methods and processes. In the examples shown, as well as with the others described herein, if the second coating 322 is employed this coating may comprise the same therapeutic agent as the base coating 320 and it may differ from the materials used for the base coating 320. In still other instances, the coatings may be applied with different concentrations in different parts of the stent 100.

FIGS. 3*a* and 3*c* show that therapeutic agent B may be applied in a higher concentration on one end 106 of the stent than on the other end 108 of the stent. Likewise, FIGS. 3*a-c* also show that therapeutic agents A, B may be applied in various concentrations throughout the thickness of the coating and along the length of the stent. The figures also show that only the base coating 320, or the base and second coatings 320, 322, may be used to contain one or more therapeutic agents. These therapeutic agents may be in the same concentration and may be in different concentrations (e.g., throughout the thickness of the coating). Still further, any number of therapeutic agents may be used.

Figure 4:
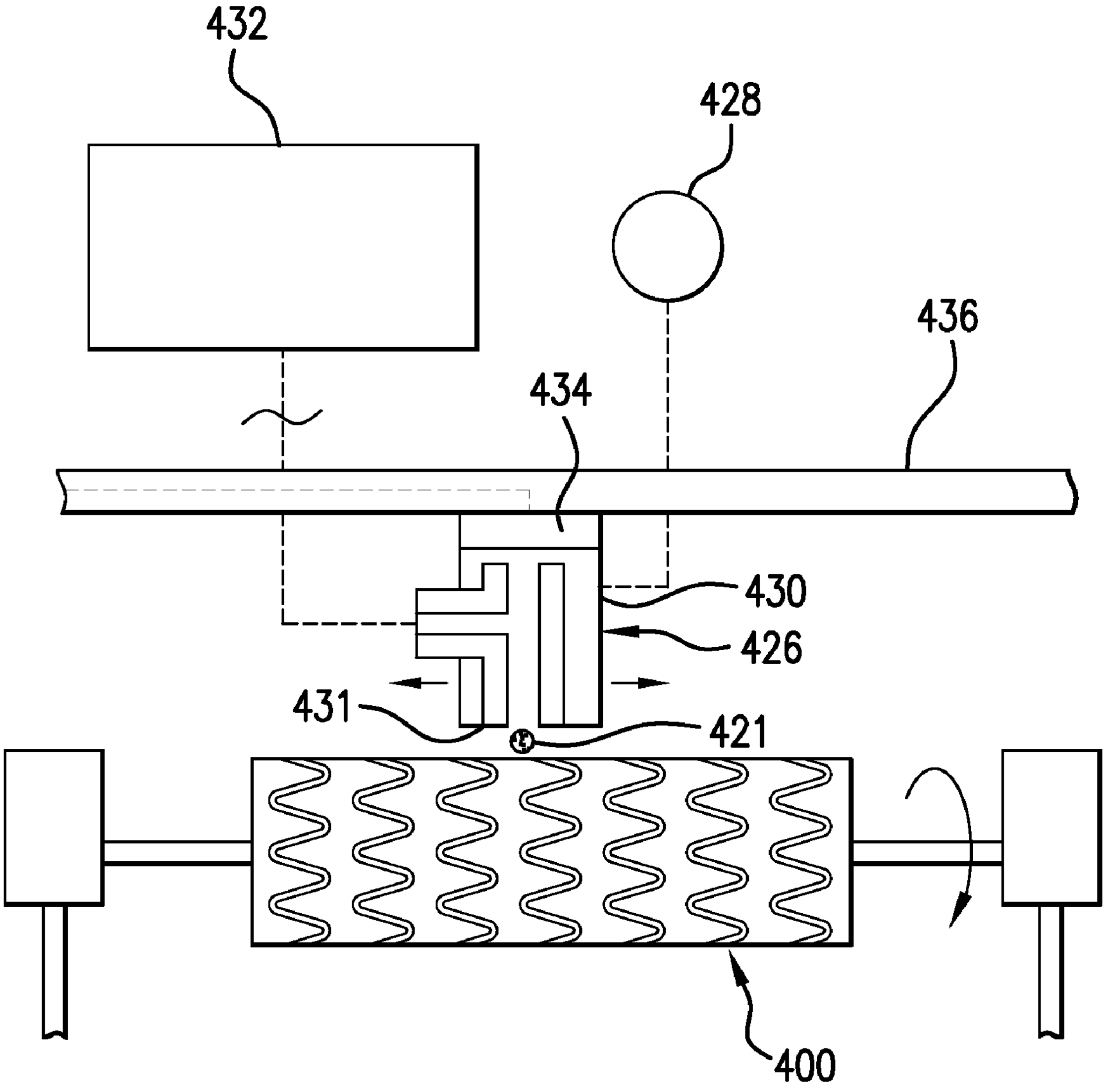
FIG. 4 shows a drop-on-demand dispensing device applying coating to a coronary stent in accordance with certain embodiments of the present invention.

FIG. 4 shows a drop-on-demand coating device 426 applying coating solution 421 to a coronary stent 400 with a base coating in accordance with certain embodiments of the present invention. Multiple coatings may be applied using the dispensing device 426 and each coating may include therapeutic agents which are the same or different from layer to layer.

The coating device 426 may be connected to a processor 428 having storage media. The processor 428 may include software which determines the optimum distribution pattern, e.g., longitudinal and/or circumferential distribution of the coating solution 421 and therapeutic agent. The software may be used to avoid or create local regions of high or low drug concentration, to target steady state elution rates and/or concentration in the center of the therapeutic agent window. The software may also be used to store the characteristics of individual and/or groups of medical devices. For example, in FIG. 4, the unique external pattern of the stent 400 may be stored to assist, cooperate, and/or instruct the dispensing device 426 during coating within precise dimensions.

In FIG. 4, the dispensing device 426 may generate energy waves to create droplets of coating including therapeutic agent and/or other coatings and eject the coating 421 droplets at a target surface of the stent 400. The dispensing device 426 may include a housing 430, a nozzle 431 in communication with a fluid reservoir 432, and an energy source 434 (e.g., a resistor or transducer) to create droplets of coating solution 421. As the droplet expands, coating solution 421 may be forced out of the nozzle 431 and directed towards a target surface of the stent 400. When the droplet collapses, if a resistor is used, a vacuum may be created, which leads to more coating solution 421 being pulled from the reservoir 432 for ejection. As discussed herein below, multiple nozzles 431 and reservoirs 432, each which may include the same or different coatings, may be used to create and eject multiple droplets of coating solutions 421 at the stent 400 depending upon the coating requirements.

The dispensing device 426 may be connected to various machine tool components for positioning the device with respect to the target surface of a medical device. The medical device may also be connected to various machine tool components for positioning target surfaces of the device with respect to the dispensing device. For example, as shown in FIG. 4, the dispensing device 426 may be connected to a track 436 that permits and facilitates longitudinal movement. Also as shown in FIG. 4, the stent 400 may be rotated by a conventional holder.

Figure 5:
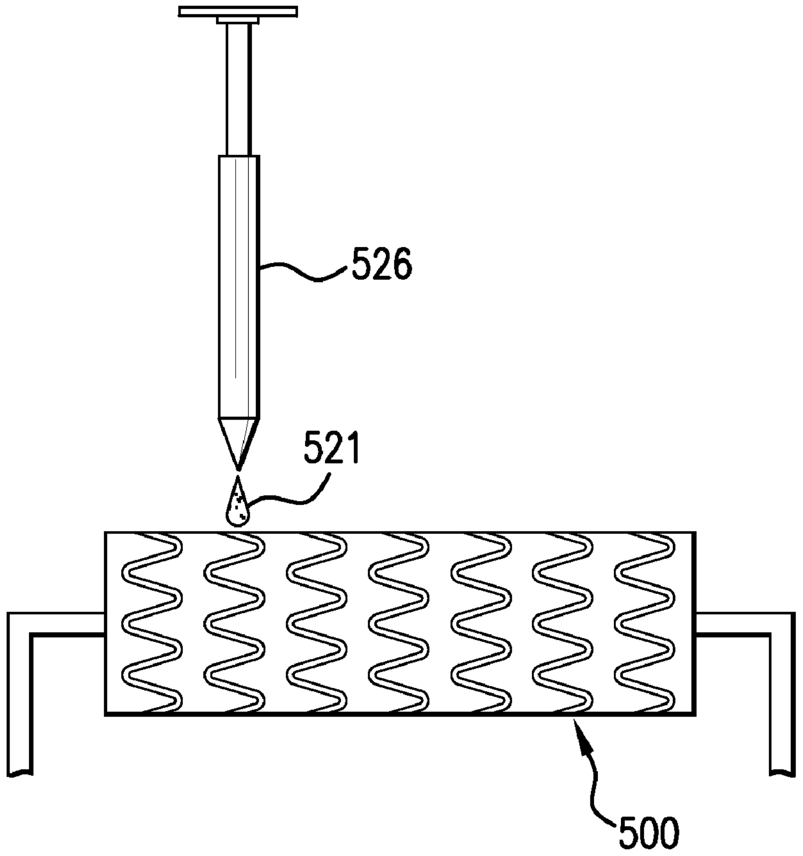
FIG. 5 shows a microinjection dispensing device applying coating to a coronary stent in accordance with certain embodiments of the present invention.

In the alternative embodiment of FIG. 5, another dispensing device 526 is shown applying coating 521 to a coronary stent 500 in accordance with certain embodiments of the present invention. The dispensing device 526 visible in FIG. 5 is a microinjection dispensing device (e.g., a micro-pipette); however, other suitable microinjection dispensing devices may be used including, but not limited to ball point and felt-tip applicators. In FIG. 5, the microinjection dispensing device 526 is connected to a reservoir(s) (not shown) and configured to eject coating 521 onto the stent 500. For example, the microinjection dispensing device 526 may be coordinated with the movement of the stent 500 to eject coating onto a unique external pattern of the stent 500 within precise dimensions. Although the microinjection dispensing device 526 is shown connected to a machine tool component, the device may also be hand-held.

Figure 6A:
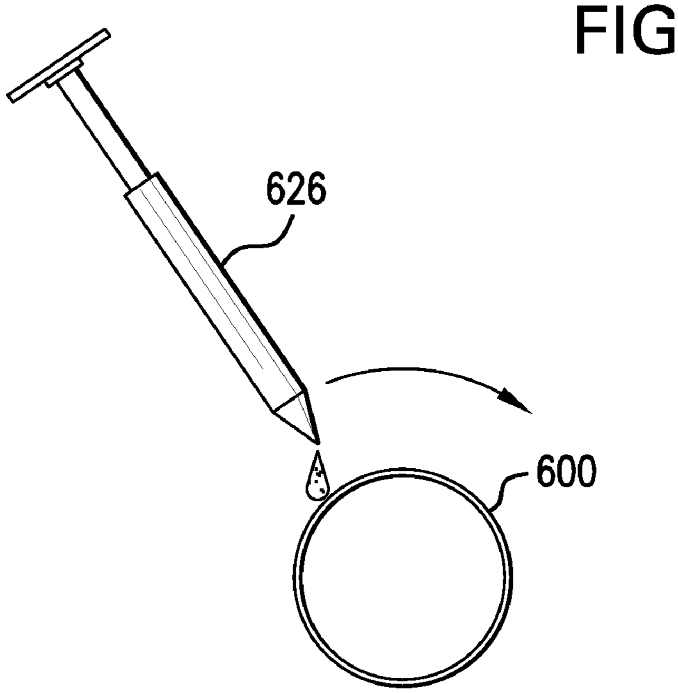
FIG. 6*a* shows the microinjection dispensing device of FIG. 5 being moved circumferentially.
Figure 6B:
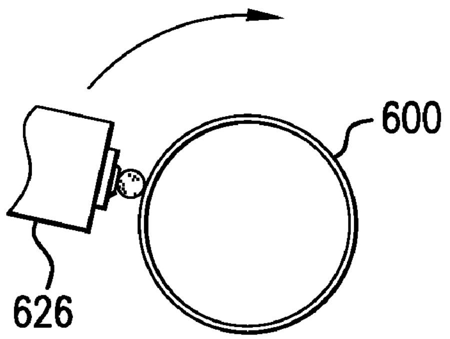
FIG. 6*b* shows the drop-on-demand dispensing device of FIG. 4 being moved circumferentially.

As seen in FIGS. 6*a*-6*b*, the dispensing devices 426, 526 of FIGS. 4-5 may be moved circumferentially and longitudinally using conventional machine tool components (e.g., tracks, gearing, robotics, flexible hoses, etc.). As seen in FIGS. 6*a*-6*b*, dispensing devices 626 are being rotated about a stent 600.

Figure 7:
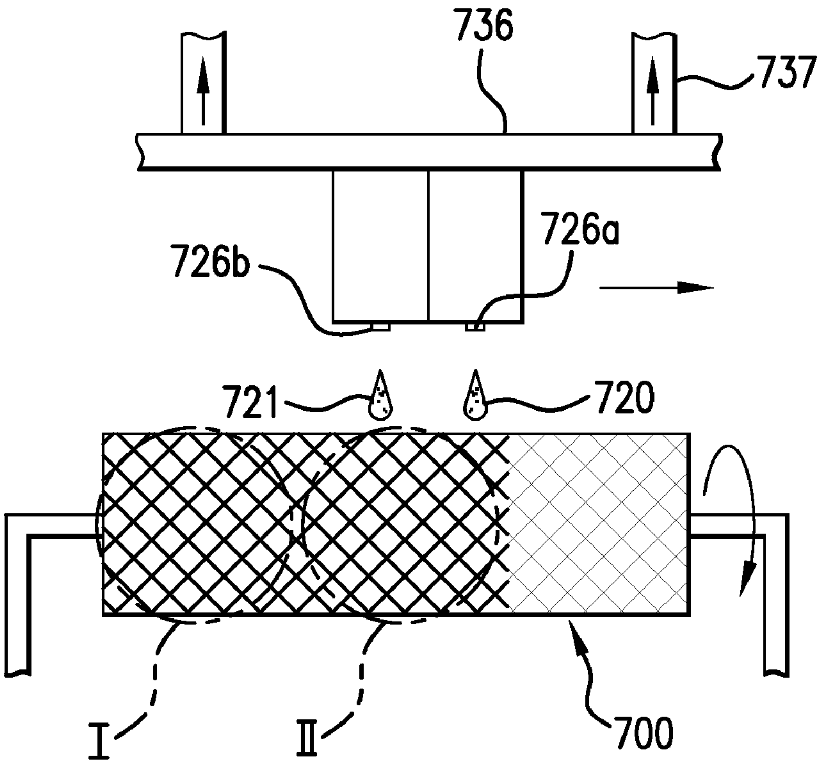
FIG. 7 shows a drop-on-demand dispensing device including two nozzles applying coating to a coronary stent in accordance with certain embodiments of the present invention.

FIG. 7 shows a drop-on-demand dispensing device 726 including two nozzles 726*a, b* applying coatings 720, 721 to a coronary stent 700 (which is being rotated) in accordance with some embodiments of the present invention. In this embodiment, the nozzles 726*a, b* are moving from right to left on a track 736. In this instance, an additional track 737 may be provided for moving the nozzles 726*a, b* up and/or down.

The coatings 720, 721 may be applied in a variety of different ways. For instance, as seen in FIG. 7, the base coating 720 and the coating solution 721 including therapeutic agent may be applied sequentially. Alternatively, the base coating 720 may be applied in the first pass, and then, following a drying time period, the coating solution 721 including therapeutic agents A and/or B may be applied in a second pass using one or more nozzles. A multitude of suitable alternative arrangements are possible.

As stated above, in this example, the leading nozzle 726*a* is applying the base coating 720. The trailing nozzle 726*b* is applying the coating solution 721 including therapeutic agent A and/or B. The coating solution 721, in this example, may be a therapeutic agent and solvent solution. The coating solution 721 may penetrate and dissolve the base coating 720 after being directed from the dispensing device 726. Any suitable solvent can be used, for example, suitable solvents include, but, are not limited to benzene, chloroform, dichloromethane, dimethylformamide (DMF), ethyl acetate, MEK, tetrahydroforum (THF), toluene, and xylene.

In any of the examples described, the coating parameters (e.g., nozzle distance, drying time, droplet size, etc.) and solvent selection may be varied to control depth of therapeutic agent penetration (linked to rate of release) and concentration of the therapeutic agent. Thus, the elution time and concentration of the therapeutic agent released to the localized area of the tissue may be improved. For example, the distance the nozzles 726*a, b* are located from the medical device and/or the time period between coating applications can be varied. Further, the size of the nozzle 726*a, b* orifice may be varied to change the droplet size (linked to rate of release). The coatings may be applied intermittently and/or multiple coatings may be applied in alternating fashion.

For instance, in some examples, percent solids in the therapeutic agent/solvent solution, droplet velocity (e.g., 0.5 to 6 m/s), droplet size (e.g., 15 to 40 micrometers diameter), and spacing (e.g., centered 5-80 micrometers apart) may be used to tailor the level of penetration of drug into the polymer base layer.

The solvent selection may be varied and can be selected such that the therapeutic agent can be completely soluble and the base coating 720 can be only partially soluble. The solvent selection may determine the outcome of depth of therapeutic agent penetration to control the rate, duration, and total dose of therapeutic agent released to a localized area of tissue of a patient. For example, the solvent selection may influence the penetration of coating.

Figure 8A:
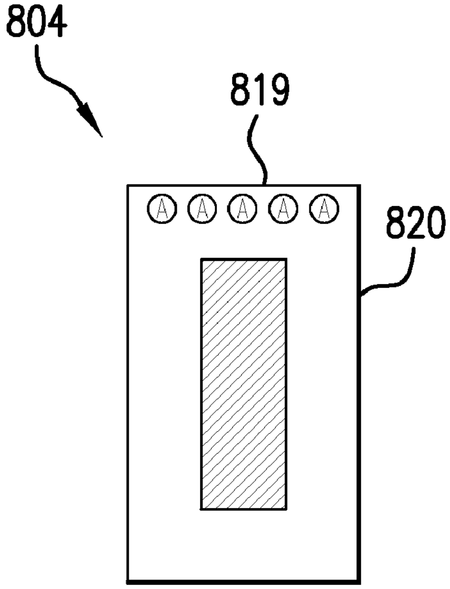
FIGS. 8*a-b* show coated coronary stent struts as may be employed in accordance with certain embodiments of the present invention.

As seen in FIG. 8*a*, a solvent may be selected such that the base coating 820 (e.g., a polymer coating) is partially soluble within the chosen solvent. For example, a partially soluble combination may be PLGA (polylactic-coglycolic-acid) and ethanol. The therapeutic agent can be dissolved in ethanol and then deposited into a PLGA polymer base coating. The ethanol may swell the PLGA to allow the therapeutic agent to diffuse into the polymer base layer. Due to the limited solubility of PLGA in ethanol, the therapeutic agent may penetrate only into the outer surface or free surface side of the polymer base coating. In accordance with certain embodiments of the present invention, the final coated medical device may include a gradient of therapeutic agent with no therapeutic agent at the medical device/polymer interface and a high concentration of therapeutic agent at the free surface of the polymer base coating.

More specifically, FIG. 8*a* shows a strut 804 conformally coated with a base coating 820 by the dispensing device of FIG. 7. In the example, therapeutic agent A may be suspended within the outer base coating 820 of the strut 804. In this example, the solvent is only partially soluble within the base coating 820, therefore, a relatively low concentration of therapeutic agent A resulted near the outer surface 819 of the base coating 820.

Figure 8B:
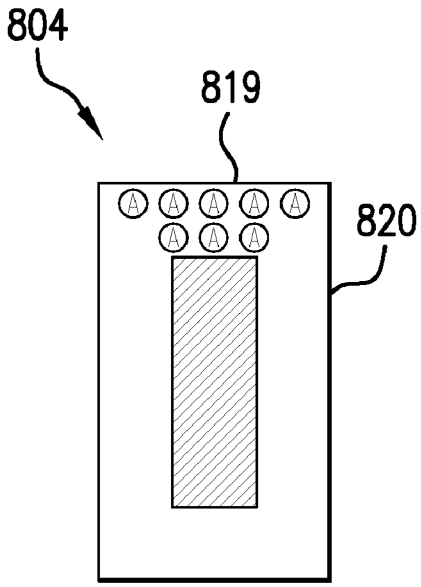

In another example shown in FIG. 8*b*, a more compatible solvent is used. An example of a more fully soluble combination may be PLGA and dimethylformamide (DMF). The therapeutic agent may be dissolved in the DMF and then deposited on a PLGA polymer base coating. Deposition of the DMF/drug solution can be uniform along the length of the stent or may vary with stent location or geometry. The DMF may solubilize the PLGA and allow the drug to be incorporated into the polymer base layer. Because of the high vapor pressure of DMF and high solubility of PLGA in DMF, the drug may be more fully incorporated into the polymer base layer. Coating parameters may be used to control the level of penetration of drug into the polymer base layer. In accordance with certain embodiments of the present invention, a gradient of therapeutic agent within the polymer may have a lower concentration at the stent/polymer interface than at the free surface of the polymer.

FIG. 8*b* shows a coated strut with a conformal base coating 820 applied with the dispensing device of FIG. 7. As seen in FIG. 8*b*, the solvent had a greater compatibility with base coating 820. Therefore, the penetration of therapeutic agent A is greater than that of FIG. 8*a*. Other arrangements are possible depending on solvent choice and coating parameters.

Figure 9A:
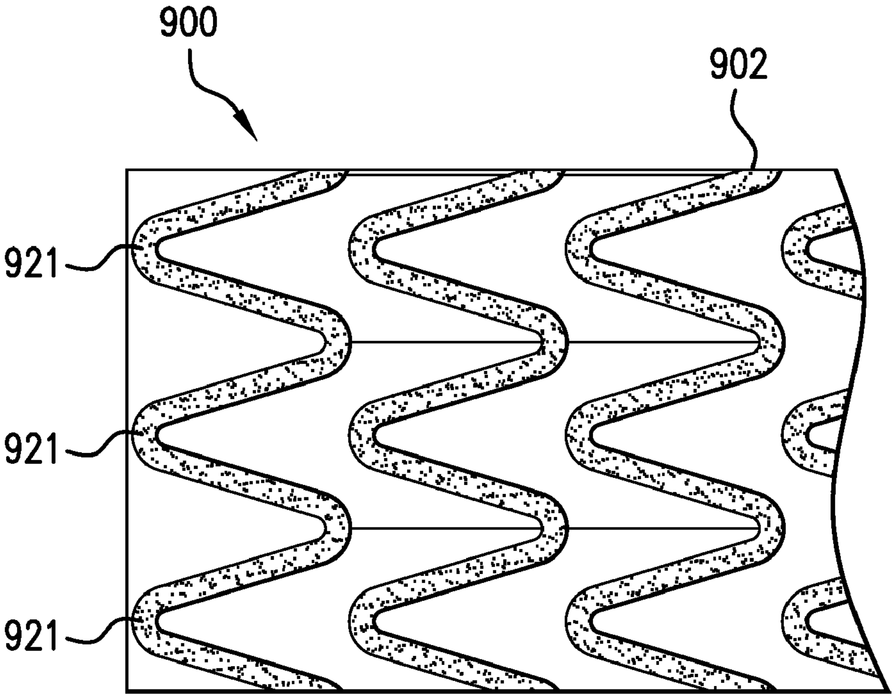
FIGS. 9*a-b* show enlarged views of portions of a coated lattice portion of a coronary stent coated with the device FIG. 7.
Figure 9B:
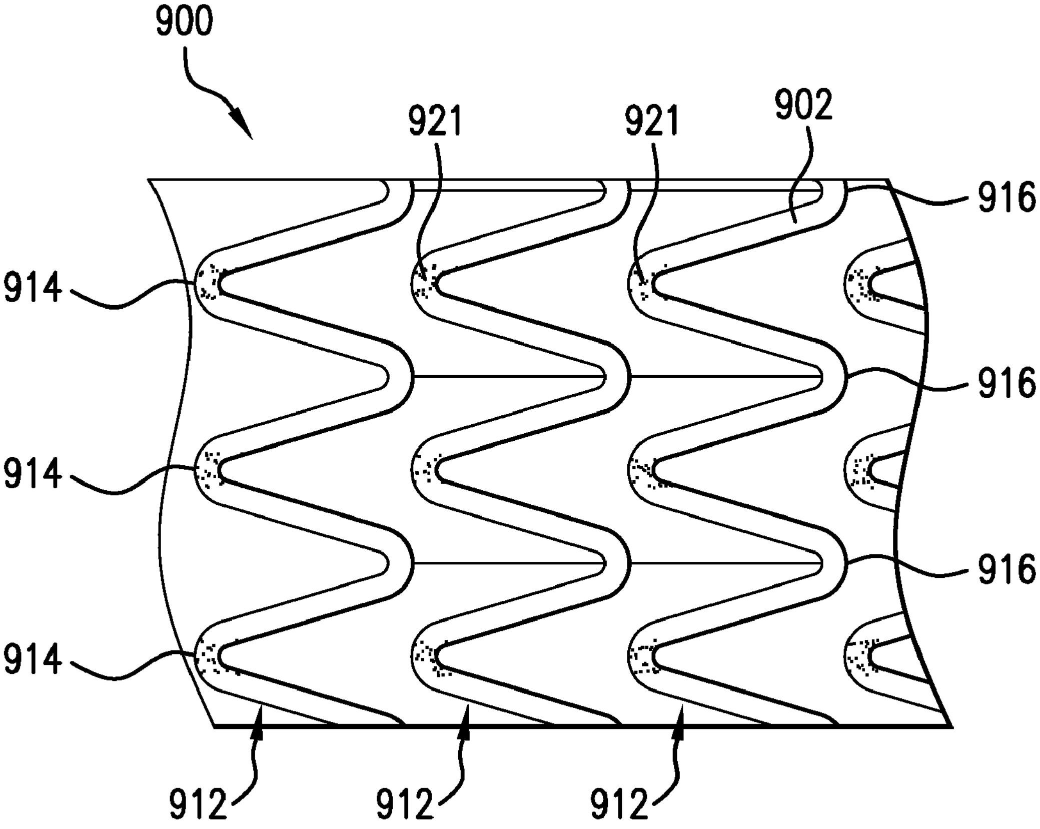

FIGS. 9*a-b* show enlarged views of portions (I and II of FIG. 7) of a stent 900 that has been coated with the dispensing device of FIG. 7. In FIG. 9*a*, which is an enlarged view of a first end (I) of the stent, it can be seen that the trailing nozzle 726*b* of FIG. 7 applied a highly concentrated amount of therapeutic agent 921 when compared to the concentration of the therapeutic agent 921 of FIG. 9*b*, which is a middle portion (II) of the stent of FIG. 7. In FIG. 9*b*, it can also be seen that only the apices 914 of the rounded bends 912 are coated. In this example, The segments 916 joining the rounded bends 912 are not coated. These examples illustrate that the distribution of coatings can be varied and/or preselected. It can be seen that the distribution of therapeutic agent A may differ from one portion (I) of the stent 900 to another portion (II). For example, therapeutic agent concentrations may be increased or decreased in specialized regions of the stent for many reasons, such as for treatment of focal lesions and carina regions of bifurcations.

Figure 10:
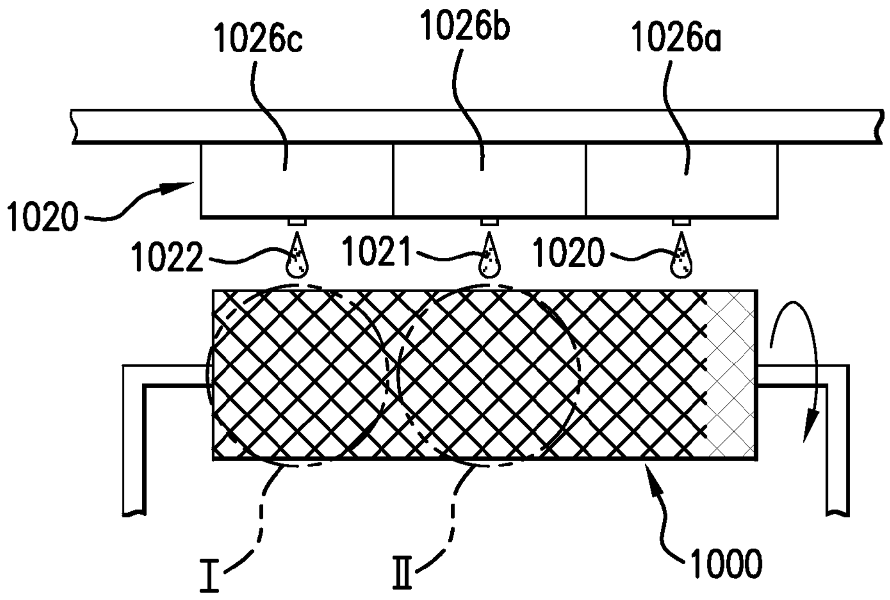
FIG. 10 shows a drop-on-demand dispensing device including three nozzles applying coating to a coronary stent in accordance with certain embodiments of the present invention.

FIG. 10 shows another drop-on-demand coating device 1026 including three nozzles 1026*a, b, c* for applying coatings 1020, 1021, 1022 to a coronary stent 1000 in accordance with yet other embodiments of the present invention. These embodiments may allow the base coating 1020, a coating solution 1021 including therapeutic agent A, and a coating solution 1022 including therapeutic agent B to be applied in one single pass or coating cycle if desired in different concentrations. For example, one nozzle 1026*a* applies the base coating 1029, a second nozzle 1026*b* applies the coating solution 1021 including therapeutic agent A and/or solvent/therapeutic agent A, and a third nozzle 1026*c* applies the coating solution 1022 including therapeutic agent B and/or therapeutic agent/solvent B. Alternatively, the base coating 1020 may be applied in the first pass, and then, following an optional drying time period, the second and third coating solutions 1021, 1022 may be applied in additional passes. Still further, a multitude of suitable alternatives are possible.

Figure 11:
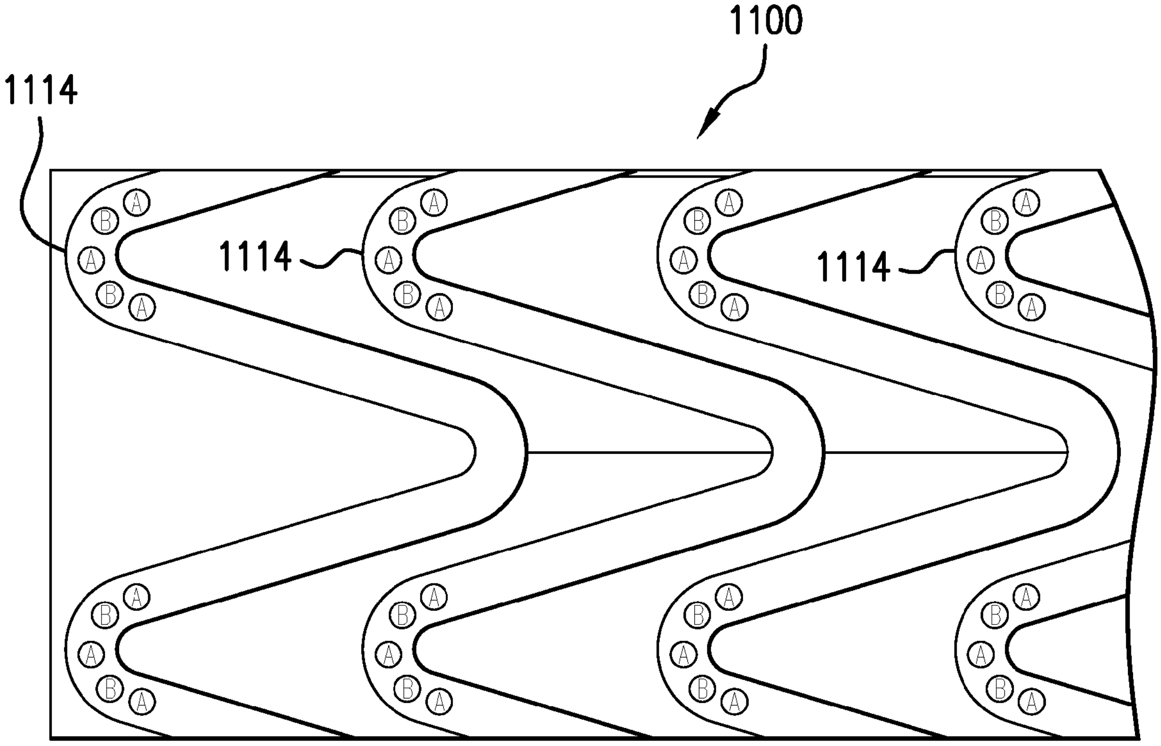
FIGS. 11-12 show enlarged views of coronary stents coated with the device of FIG. 10.
Figure 12:
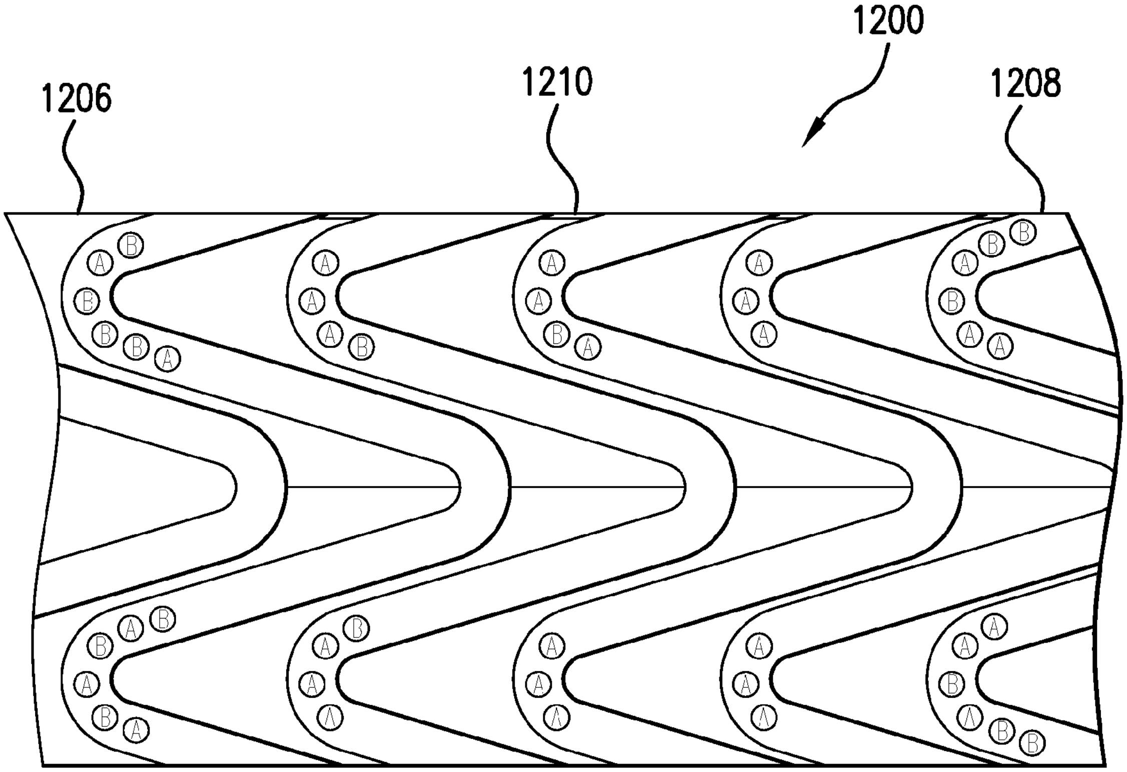

FIGS. 11-12 show views of coated stents 1100, 1200 that have been coated with the dispensing device of FIG. 10. In FIG. 11 it can be seen that only the apices 1014 of the rounded bends are coated with coatings including therapeutic agent A and B. It can also be seen that the second and third nozzles 1026*a, b* may be used to vary the concentration of therapeutic agents A, B over the length of the stent as desired. For example, as shown in FIG. 12 higher concentrations of therapeutic agent B are located on the first and second ends 1206, 1208 of the stent 1200. Moreover, higher concentrations of therapeutic agent A are deposited in the middle portion 1210 of the stent 1200.

Figure 13A:
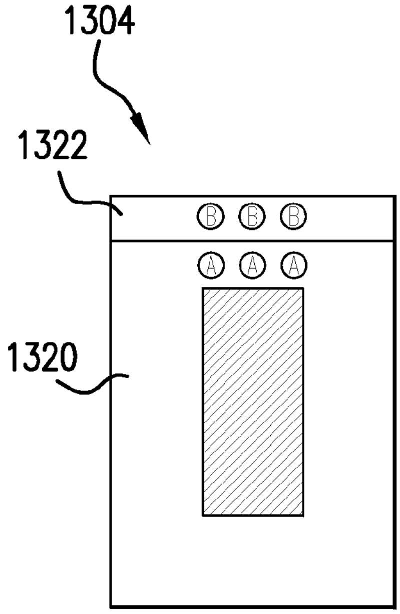
FIGS. 13*a-b* show stent struts coated with the device of FIG. 10.
Figure 13B:
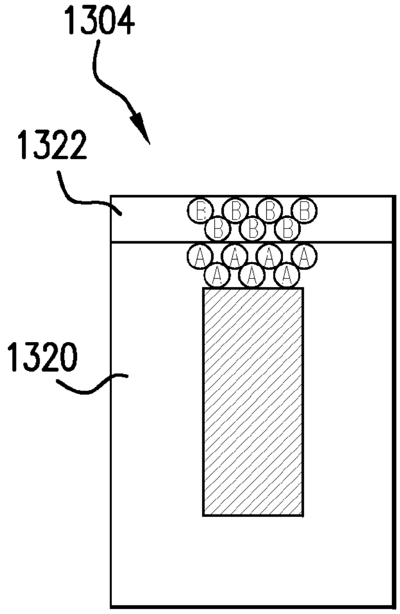

FIGS. 13a-b show struts 1304 that may be coated with the nozzles of FIG. 10. In these examples, which show enlarged views of a portions of stent struts of sections I and II of FIG. 10, the base coating 1320, including therapeutic agent A in the abluminal portion, is applied conformally, and the second coating 1322, including therapeutic agent B, may be applied abluminally. Other arrangements are also possible, for instance, therapeutic agent A can also be applied conformally in the base and second coating 1320, 1322 may be applied conformally. Likewise, therapeutic agents A and B may be provided in each coating 1320, 1322.

Also in these examples, it can be seen that concentration of therapeutic agent differs. In FIG. 13a, the solvent used with therapeutic agents A and B is only partially soluble within the base coating 1320, therefore, a relatively low concentration of therapeutic agents A and B resulted. In FIG. 13b, the solvents had a greater compatibility with the base coating and second coatings 1320, 1322. Therefore, the concentration and penetration of therapeutic agents A and B may be greater than that of FIG. 13a. Other arrangements are possible depending on solvent choice and coating parameters.

FIG. 14 shows method steps that may be employed with certain embodiments of the present invention for coating an implantable medical device. In the example of FIG. 14, step 100 of the method includes providing an implantable medical device. Step 200 applying a polymer base coating to the medical device. Step 300 can include directing a solution including therapeutic agent and solvent through the at least one nozzle onto at least one target zone of the polymer base coating to penetrate the polymer base coating, the solution being directed at the at least one target zone until a predetermined concentration of the therapeutic agent is integrated within the polymer base coating.

The sequence of steps described herein may be reordered and steps may be added or removed. The steps may also be modified. Further, the steps may be repeated in continuous fashion.

While various embodiments have been described, other embodiments are plausible. It should be understood that the foregoing descriptions of various examples of the medical device and delivery devices are not intended to be limiting, and any number of modifications, combinations, and alternatives of the examples may be employed to facilitate the effectiveness of delivering therapeutic agent to a medical device.

The coating, in accordance with the certain embodiments of the present invention, may comprise a polymeric and or therapeutic agent formed, for example, by admixing a drug agent with a liquid polymer, in the absence of a solvent, to form a liquid polymer/drug agent mixture. A suitable list of drugs and/or polymer combinations is listed below. The term "therapeutic agent" as used herein includes one or more "therapeutic agents" or "drugs". The terms "therapeutic agents" or "drugs" can be used interchangeably herein and include pharmaceutically active compounds, nucleic acids with and without carrier vectors such as lipids, compacting agents (such as histones), viruses (such as adenovirus, andenoassociated virus, retrovirus, lentivirus and α-virus), polymers, hyaluronic acid, proteins, cells and the like, with or without targeting sequences.

Specific examples of therapeutic agents used in conjunction with the present invention include, for example, pharmaceutically active compounds, proteins, cells, oligonucleotides, ribozymes, anti-sense oligonucleotides, DNA compacting agents, gene/vector systems (i.e., any vehicle that allows for the uptake and expression of nucleic acids), nucleic acids (including, for example, recombinant nucleic acids; naked DNA, cDNA, RNA; genomic DNA, cDNA or RNA in a non-infectious vector or in a viral vector and which further may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral, liposomes and cationic and anionic polymers and neutral polymers that are selected from a number of types depending on the desired application. Non-limiting examples of virus vectors or vectors derived from viral sources include adenoviral vectors, herpes simplex vectors, papilloma vectors, adeno-associated vectors, retroviral vectors, and the like. Non-limiting examples of biologically active solutes include anti-thrombogenic agents such as heparin, heparin derivatives, urokinase, and PPACK (dextrophenylalanine proline arginine chloromethylketone); antioxidants such as probucol and retinoic acid; angiogenic and anti-angiogenic agents and factors; anti-proliferative agents such as enoxaprin, angiopeptin, rapamycin, angiopeptin, monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, acetyl salicylic acid, and mesalamine; calcium entry blockers such as verapamil, diltiazem and nifedipine; antineoplastic/antiproliferative/anti-mitotic agents such as paclitaxel, 5-fluorouracil, methotrexate, doxorubicin, daunorubicin, cyclosporine, cisplatin, vinblastine, vincristine, epothilones, endostatin, angiostatin and thymidine kinase inhibitors; antimicrobials such as triclosan, cephalosporins, aminoglycosides, and nitrofurantoin; anesthetic agents such as lidocaine, bupivacaine, and ropivacaine; nitric oxide (NO) donors such as linsidomine, molsidomine, L-arginine, NO-protein adducts, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warfarin sodium, Dicumarol, aspirin, prostaglandin inhibitors, platelet inhibitors and tick antiplatelet factors; vascular cell growth promoters such as growth factors, growth factor receptor antagonists, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vascoactive mechanisms; survival genes which protect against cell death, such as anti-apoptotic Bcl-2 family factors and Akt kinase; and combinations thereof. Cells can be of human origin (autologous or allogenic) or from an animal source (xenogeneic), genetically engineered if desired to deliver proteins of interest at the insertion site. Any modifications are routinely made by one skilled in the art.

Polynucleotide sequences useful in practice of the invention include DNA or RNA sequences having a therapeutic effect after being taken up by a cell. Examples of therapeutic agent polynucleotides include anti-sense DNA and RNA; DNA coding for an anti-sense RNA; or DNA coding for tRNA or rRNA to replace defective or deficient endogenous molecules. The polynucleotides can also code for therapeutic proteins or polypeptides. A polypeptide is understood to be any translation product of a polynucleotide regardless of size, and whether glycosylated or not. Therapeutic proteins and polypeptides include as a primary example, those proteins or polypeptides that can compensate for defective or deficient species in an animal, or those that act through toxic effects to limit or remove harmful cells from the body. In addition, the polypeptides or proteins that can be injected, or whose DNA can be incorporated, include without limitation, angiogenic factors and other molecules competent to induce angiogenesis, including acidic and basic fibroblast growth factors, vascular endothelial growth factor, hif-1, epidermal growth factor, transforming growth factor $\alpha$ and $\beta$, platelet-derived endothelial growth factor, platelet-derived growth factor, tumor necrosis factor $\alpha$, hepatocyte growth factor and insulin like growth factor; growth factors; cell cycle inhibitors including CDK inhibitors; anti-restenosis agents, including p15, p16, p18, p19, p21, p27, p53, p57, Rb, nFkB and E2F decoys, thymidine kinase ("TK") and combinations thereof and other agents useful for interfering with cell proliferation, including agents for treating malignancies; and combinations thereof. Still other useful factors, which can be provided as polypeptides or as DNA encoding these polypeptides, include monocyte chemoattractant protein ("MCP-1"), and the family of bone morphogenic proteins ("BMPs"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMPs are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNAs encoding them.

As stated above, coatings used with the certain embodiments of the present invention may comprise a polymeric material/drug agent matrix formed, for example, by admixing a drug agent with a liquid polymer, in the absence of a solvent, to form a liquid polymer/drug agent mixture. Curing of the mixture typically occurs in-situ. To facilitate curing, a cross-linking or curing agent may be added to the mixture prior to application thereof. Addition of the cross-linking or curing agent to the polymer/drug agent liquid mixture must not occur too far in advance of the application of the mixture in order to avoid over-curing of the mixture prior to application thereof. Curing may also occur in-situ by exposing the polymer/drug agent mixture, after application to the luminal surface, to radiation such as ultraviolet radiation or laser light, heat, or by contact with metabolic fluids such as water at the site where the mixture has been applied to the luminal surface. In coating systems employed in conjunction with the present invention, the polymeric material may be either bioabsorbable or biostable. Any of the polymers described herein that may be formulated as a liquid may be used to form the polymer/drug agent mixture.

In accordance with the certain embodiments, the polymer used to coat the medical device is provided in the form of a coating on an expandable portion of a medical device. After applying the drug solution to the polymer and evaporating the volatile solvent from the polymer, the medical device is inserted into a body lumen where it is positioned to a target location. In the case of a balloon catheter, the expandable portion of the catheter is subsequently expanded to bring the drug-impregnated polymer coating into contact with the lumen wall. This enables administration of the drug to be site-specific, limiting the exposure of the rest of the body to the drug.

The polymer used in the exemplary embodiments of the present invention is preferably capable of absorbing a substantial amount of drug solution. When applied as a coating on a medical device in accordance with the present invention, the dry polymer is typically on the order of from about 1 to about 50 microns thick. In the case of a stent, the thickness is preferably about 1 to 10 microns thick, and more preferably about 2 to 5 microns. Very thin polymer coatings, e.g., of about 0.2-0.3 microns and much thicker coatings, e.g., more than 50 microns, are also possible. It is also within the scope of the present invention to apply multiple layers of polymer coating onto a medical device. Such multiple layers are of the same or different polymer materials.

The polymer of the present invention may be hydrophilic or hydrophobic, and may be selected from the group consisting of polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof as well as other biodegradable, bioabsorbable and biostable polymers and copolymers. Coatings from polymer dispersions such as polyurethane dispersions (BAYHYDROL®, etc.) and acrylic latex dispersions are also within the scope of the present invention. The polymer may be a protein polymer, fibrin, collagen and derivatives thereof, polysaccharides such as celluloses, starches, dextrans, alginates and derivatives of these polysaccharides, an extracellular matrix component, hyaluronic acid, or another biologic agent or a suitable mixture of any of these, for example. In one embodiment of the invention, the preferred polymer is polyacrylic acid, available as HYDROPLUS® (Boston Scientific Corporation, Natick, Mass.), and described in U.S. Pat. No. 5,091,205, the disclosure of which is hereby incorporated herein by reference. U.S. Pat. No. 5,091,205 describes medical devices coated with one or more polyisocyanates such that the devices become instantly lubricious when exposed to body fluids. In another preferred embodiment of the invention, the polymer is a copolymer of polylactic acid and polycaprolactone.

The examples described herein are merely illustrative, as numerous other embodiments may be implemented without departing from the spirit and scope of the exemplary embodiments of the present invention. Moreover, while certain features of the invention may be shown on only certain embodiments or configurations, these features may be exchanged, added, and removed from and between the various embodiments or configurations while remaining within the scope of the invention. Likewise, methods described and disclosed may also be performed in various sequences, with some or all of the disclosed steps being performed in a different order than described while still remaining within the spirit and scope of the present invention.

What is claimed is:

1. A method of coating an implantable medical device in at least a two-step coating process, the method comprising:
providing an implantable medical device;
applying a polymer base coating to the medical device in a first step; and
in a second separate step, directing a solution including therapeutic agent and solvent through at least one nozzle onto at least one target zone of the polymer base coating to penetrate the polymer base coating, the solution being directed at the at least one target zone until a predetermined concentration of the therapeutic agent is integrated within the polymer base coating.

2. The method of claim 1, wherein the solvent fully dissolves the polymer base coating so that the therapeutic agent penetrates the entire thickness of the polymer base coating.

3. The method of claim 1, further comprising directing a second solution including a second therapeutic agent and second solvent through the at least one nozzle, the second solution being directed at the at least one target zone until a predetermined concentration of the second therapeutic agent is integrated within the polymer base coating.

4. The method of claim 3, wherein the second solvent partially dissolves the polymer base coating so that the second therapeutic agent penetrates only a surface portion of the polymer base coating.

5. The method of claim 3, wherein the second therapeutic agent is different than the first therapeutic agent.

6. The method of claim 1, wherein a second polymer base coating is applied to an outer surface of the polymer base coating.

7. The method of claim 6, further comprising directing a second solution including a second therapeutic agent and second solvent through the at least one nozzle, the second solution being directed at a second target zone of the second polymer base coating to penetrate the second polymer base coating, the solution being directed at the second target zone until a predetermined concentration of the second therapeutic agent is integrated within the second polymer base coating.

8. The method of claim 7, wherein the second therapeutic agent is different than the first therapeutic agent.

9. The method of claim 1, wherein the at least one nozzle is part of a delivery device, wherein the delivery device is a drop-on-demand device including the at least one nozzle in communication with a reservoir, a housing, and an energy source.

10. The method of claim 1, wherein the implantable medical device is a stent.

11. The method of claim 10, wherein the step of directing a solution including therapeutic agent and solvent onto at least one target zone comprises selectively directing the solution onto the polymer base coating to create a desired therapeutic agent distribution across the stent.

12. The method of claim 11, wherein desired therapeutic agent distribution includes higher concentrations of therapeutic agent at some areas of the stent as compared to other areas of the stent.

13. A method of coating an implantable medical device in at least a two-step coating process, the method comprising:
providing an implantable medical device; positioning a delivery device having first, second, and third nozzles proximate to the medical device;
applying a polymer base coating through the first nozzle to the medical device in a first step;
in a second separate step, directing a first solution including therapeutic agent and solvent through the second nozzle onto at least one target zone of the polymer base coating to penetrate the polymer base coating, the solution being directed at the at least one target zone until a predetermined concentration of the therapeutic agent is integrated within the polymer base coating; and
directing a second solution including a second therapeutic agent and second solvent through the third nozzle, the second solution being directed at the at least one target zone until a predetermined concentration of the second therapeutic agent is integrated within the polymer base coating.

14. A method of coating a stent in at least a two-step coating process, the method comprising:
providing a stent having a lattice comprised of a plurality of struts, each strut having an inner surface, an outer surface, and a plurality of cut faces;
applying a polymer base coating onto a target portion of the lattice portion in a first step; and
in a second separate step, directing a solution including therapeutic agent and solvent towards at least one first target zone of the polymer base coating to penetrate the polymer base coating, the solution being directed at the at least one first target zone until a predetermined concentration of the therapeutic agent is integrated within the polymer base coating.

15. The method of claim 14, further comprising directing a second solution including a second therapeutic agent and second solvent toward at least one second target zone until a predetermined concentration of the second therapeutic agent is integrated within the polymer base coating.

16. The method of claim 15, wherein the first therapeutic agent is deposited throughout substantially all of the polymer base coating, and wherein the second therapeutic agent is deposited within the polymer base coating only on an abluminal side of the stent.

17. The method of claim 15, wherein the first therapeutic agent is deposited through a greater thickness of the polymer base coating than the second therapeutic agent.

18. The method of claim 15, wherein the first therapeutic agent is deposited along substantially the entire length of the stent and wherein the second therapeutic agent is deposited only on one or both ends of the stent.

19. The method of claim 14, wherein the polymer base coating is applied to the outer surface of each strut of the target portion.

20. The method of claim 14, wherein the polymer base coating is applied to the inner and outer surfaces and cut faces of each strut of the target portion.

21. The method of claim 20, wherein a second polymer base coating is applied to the outer surface of each strut.

22. The method of claim 20, further comprising directing a second solution including a second therapeutic agent and second solvent towards a second target zone of the second polymer base coating to penetrate the second polymer base coating, the solution being directed at the second target zone until a predetermined concentration of the second therapeutic agent is integrated within the second polymer base coating.

23. The method of claim 14, wherein the lattice includes rounded bends having apices, the rounded bends are joined by segments, and wherein the therapeutic agent concentration is larger in the apices than in the segments.

* * * * *